United States Patent [19]
Curotto et al.

[11] Patent Number: 5,733,867
[45] Date of Patent: Mar. 31, 1998

[54] 1, 5-BENZODIAZEPINE DERIVATIVES

[75] Inventors: Giovanni Curotto; Mario Pellegatti; Stefano Polinelli, all of Verona, Italy

[73] Assignee: Glaxo Wellcome SpA, Verona, Italy

[21] Appl. No.: 578,534

[22] PCT Filed: Jul. 18, 1994

[86] PCT No.: PCT/EP94/02352

§ 371 Date: Nov. 4, 1996

§ 102(e) Date: Nov. 4, 1996

[87] PCT Pub. No.: WO95/03284

PCT Pub. Date: Feb. 2, 1995

[30] Foreign Application Priority Data

Jul. 20, 1993 [GB] United Kingdom ........... 9315018

[51] Int. Cl.⁶ .................... C07D 243/12; A61K 31/55
[52] U.S. Cl. .................................... 512/221; 540/518
[58] Field of Search ........................ 540/518; 514/221

[56] References Cited

FOREIGN PATENT DOCUMENTS

| | | | |
|---|---|---|---|
| A-0 376 849 | 7/1990 | European Pat. Off. | C07D 243/12 |
| A-93 14074 | 7/1993 | WIPO | C07D 243/12 |
| A-93 14075 | 7/1993 | WIPO | C07D 243/12 |
| 03254 | 2/1995 | WIPO | C07D 243/12 |

*Primary Examiner*—Robert T. Bond
*Attorney, Agent, or Firm*—Bacon & Thomas

[57] ABSTRACT

Compounds of general formula (I)

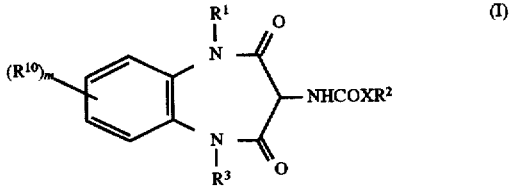

wherein
$R^1$ represents a phenyl, $C_{3-7}$cycloalkyl, $C_{7-11}$bridgedcycloalkyl or $C_{1-6}$alkyl group which alkyl group may be substituted by a hydroxy, phenyl, $C_{1-6}$alkoxycarbonyl, $C_{3-7}$cycloalkyl, or $C_{3-7}$bridgedcycloalkyl group;

$R^2$ represents phenyl substituted by a group $(CH_2)_n NR^4R^5$, $O(CH_2)_p R^6$, or $(CH_2)_n CO_2 R^{11}$;

$R^3$ represents phenyl optionally substituted by one or 2 halogen atoms;

$R^4$ represents hydrogen or $C_{1-4}$alkyl;

$R^5$ represents acyl, or $C_{2-4}$alkyl substituted by one or more hydroxy; carboxyl and/or amino groups or $R^4$ and $R^5$ together with the nitrogen atom to which they are attached form a 5–7 saturated heterocyclic ring which contain an additional heteroatom selected from oxygen, sulphur or nitrogen and/or may be substituted by 1 or 2 $C_{1-4}$alkyl or hydroxy groups.

$R^6$ represents hydroxy, $C_{1-4}$alkoxy, $CO_2R^7$ or $NR^8R^9$;

$R^7$ represents hydrogen or $C_{1-4}$alkyl or a metabolically labile ester group;

$R^8$ represents hydrogen, $C_{1-4}$, acyl or $C_{2-6}$alkyl substituted by one or more hydroxy, carboxyl and/or amino groups or $R^8$ and $R^9$ together with the nitrogen atom to which they are attached form a 5–7 saturated heterocyclic ring which contain an additional heteroatom selected from oxygen, sulphur or nitrogen and/or may be substituted by 1 or 2 $C_{1-4}$alkyl or hydroxy groups;

$R^{10}$ represents hydrogen or a halogen atom; $R^{11}$ represents a metabolically labile ester group; m is zero, 1 or 2;

n is zero or 1; p is an integer from 1 to 4; X represents oxygen or NH and pharmaceutically acceptable, salts thereof are antagonists of gastrin and CCK.

10 Claims, No Drawings

1, 5-BENZODIAZEPINE DERIVATIVES

This application is a 371 of PCT/EP 94/02352, filed Jul. 18, 1994, which claims priority of British Application 9315018.3 filed 26 Jul. 1993.

This invention relates to novel 1,5-benzodiazepine derivatives, to processes for their preparation, to pharmaceutical compositions containing them and to their use in medicine.

Cholecystokinins (CCK) and gastrin are structurally related peptides which exist in gastrointestinal tissue and in the central nervous system. Cholecystokinins include CCK-33, a neuropeptide to thirty-three amino acids in its originally isolated forms, its carboxy terminal octapeptide sulphate, CCK-8 (also a naturally-occurring neuropeptide), and 39- and 12-amino acid forms. Gastrin occurs in 34-, 17- and 14- amino acid forms, with the minimum active sequence being the C-terminal tetrapeptide, Trp-Met-Asp-Phe-NH$_2$(CCK-4), which is the common structual element shared by both CCK and gastrin.

CCK and gastrin are gastrointestinal hormones and neurotransmitters in the neural and peripheral systems and perform their respective biological roles by binding to particular receptors located at various sites throughout the body.

There are at least two subtypes of cholecystokinin receptors termed CCK-A and CCK-B and both are found in the periphery and in the central nervous system. CCK and gastrin receptor antagonists have been disclosed for preventing and treating CCK-related and/or gastrin related disorders of the gastrointestinal and central nervous systems of animals, and more particularly humans.

U.S. Pat. No. 4,988,692 describes a group of 3-acylamino 1-alkyl-5-phenyl 1,5-benzodiazepine derivatives as cholecystokinin antagonists. Further the specification teaches that the compounds have a significantly greater affinity for the CCK-A receptor over the CCK-B receptor.

We have now found a novel group of 3-substituted 1,5-benzodiazepine compounds which are potent and specific antagonists of gastrin and/or CCK and in particular antagonists of gastrin and/or CCK at the CCK-B receptor which exhibit a particularly advantageous profile of activity.

Thus, the invention provides compounds of general formula (I)

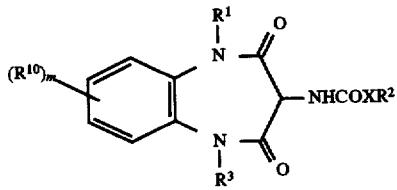

wherein

R$^1$ represents a phenyl, C$_{3-7}$cycloalkyl, C$_{7-11}$bridgedcycloalkyl or C$_{1-6}$alkyl group which alkyl group may be substituted by a hydroxy, phenyl, C$_{1-6}$alkoxycarbonyl, C$_{3-7}$cycloalkyl, or C$_{3-7}$bridgedcycloalkyl group;

R$^2$ represents phenyl substituted by a group (CH$_2$)$_n$NR$^4$R$^5$, O(CH$_2$)$_p$R$^6$, or (CH$_2$)$_n$CO$_2$R$^{11}$;

R$^3$ represents phenyl optionally substituted by one or 2 halogen atoms;

R$^4$ represents hydrogen or C$_{1-4}$alkyl;

R$^5$ represents acyl, or C$_{2-4}$alkyl substituted by one or more hydroxy; carboxyl and/or amino groups or R$^4$ and R$^5$ together with the nitrogen atom to which they are attached form a 5-7 saturated heterocyclic ring which contain an additional heteroatom selected from oxygen, sulphur or nitrogen and/or may be substituted by 1 or 2 C$_{1-4}$alkyl or hydroxy groups.

R$^6$ represents hydroxy, C$_{1-4}$alkoxy, CO$_2$R$^7$ or NR$^8$R$^9$;

R$^7$ represents hydrogen or C$_{1-4}$alkyl or a metabolically labile ester group;

R$^8$ represents hydrogen, C$_{1-4}$, acyl or C$_{2-6}$alkyl substituted by one or more hydroxy, carboxyl and/or amino groups or R$^8$ and R$^9$ together with the nitrogen atom heterocylic group examples of suitable groups include morpholino, to which they are attached form a 5-7 saturated heterocyclic ring which contain an additional heteroatom selected from oxygen, sulphur or nitrogen and/or may be substituted by 1 or 2 C$_{1-4}$alkyl or hydroxy groups;

R$^{10}$ represents hydrogen or a halogen atom; R$^{11}$ represents a metabolically labile ester group; m is zero, 1 or 2;

n is zero or 1; p is an integer from 1 to 4; X represents oxygen or NH and pharmaceutically acceptable salts thereof.

It will be appreciated that compounds of formula (I) possess at least one asymmetric carbon atom (namely the carbon atom occupying the 3-position of the diazepine ring) and the compounds of the invention thus include all stereoisomers and mixtures thereof including the racemates.

In the compounds of formula (I) 'alkyl' when used as a substituent or part of a substituent group means that the group may be straight or branched. Thus, C$_{1-6}$alkyl includes methyl, ethyl, n-propyl, isopropyl, n-butyl, isobutyl or tert-butyl, n-pentyl, isopentyl, neopentyl, n-hexyl, isohexyl, 1,3-dimethylbutyl, 3,3-dimethylbutyl, 2,3-dimethylbutyl.

For the group R$^1$ the term C$_{3-7}$cycloalkyl as a group or part of a group refers to a monocyclic alkyl group such as cyclopropyl, cylobutyl, cyclopentyl, cyclohexyl or cycloheptyl. The term C$_{7-11}$bridged cycloalkyl refers to groups such adamantyl, norbornanyl or norbornenyl.

For the groups R$^4$, R$^5$, R$^7$ R$^8$ and R$^9$ the term C$_{1-4}$alkyl includes 3-4-cycloalkyl (e.g) cyclopropyl or cyclobutyl) as well as straight or branched chain alkyl groups as defined above.

Halogen in the definition of compounds of formula (I) may represent a fluoro, chloro, bromo or iodo substituent.

When R$^2$ is a phenyl group substituted by a single substituent this may be in the ortho, or more preferably in the meta or para position.

When the group R$^4$ and R$^5$ together with the nitrogen atom represent a saturated heterocylic group examples of suitable groups include morpholino, 2,6-dimethylmorpholino, thiomorpholino, piperidino, 4,4-dimethylpiperidino and pyrrolidino.

When R$^5$ represents acyl this may be for example C$_{1-6}$alkanoyl e.g. formyl or acetyl.

When R$^5$ represents C$_{2-4}$alkyl substituted by one or more hydroxyl groups examples of such groups include 2-hydroxyethyl, 3-hydroxpropyl, 2-hydroxypropyl or 2,3-dihydroxypropyl.

When R$^8$ and R$^9$ together with the nitrogen atom to which they are attached represent an heterocylic group examples of suitable groups include morpholino, 2,6-dimethylmorpholino, piperidino, pyrrolidino, piperazino or N-methylpiperazino.

When R$^{10}$ is halogen this is preferably chlorine or fluorine.

When m is 1 or 2 the halogen atom(s) e.g. chlorine or fluorine are preferably in the 7 and/or 8 positions.

When $R^1$ represents an alkyl group substituted by a hydroxyl group this is preferably a $C_{3-6}$alkyl group substituted by hydroxy. Examples of such groups include 2-hydroxypropyl, 2-hydroxy-3-methylbutyl and 2-hydroxy-3,3-dimethylbutyl of which 2-hydroxy-3-methylbutyl, and 2-hydroxy-3,3-dimethylbutyl are particularly preferred.

When $R^1$ represent an alkyl group substituted by a $C_{3-7}$cycloalkyl group this is preferably a $C_{2-3}$alkyl group such as ethyl or 1-methylethyl, substituted by a $C_{3-7}$cycloalkyl group such as cyclopentyl or $R^1$ represents cyclohexylmethyl.

When $R^1$ is a bridged $C_{7-11}$cycloalkyl group this may be for example an adamantyl group such as 1-adamantyl or 2-adamantyl group or a 2-norbornanyl group.

When $R^1$ is an alkyl group substituted by a bridged $C_{7-11}$cycloalkyl group this is preferably an ethyl group or more especially a methyl group substituted by a bridged $C_{7-11}$cycloalkyl group. Examples of suitable briged cycloalkyl groups include adamantyl such as 1-adamantyl or 2-adamantyl, 2-norbornanyl or 5-norbornenyl. Most preferably $R^1$ represents 1-adamantylmethyl.

When $R^1$ is alkyl substituted by phenyl this may be for example benzyl or phenethyl.

When $R^1$ is alkyl substituted by alkoxycarbonyl this is preferably methyl substituted by alkoxycarbonyl such methoxycarbonyl or as t-butoxycarbonyl.

A preferred class of compounds of formula (I) is that in which $R^1$ represents a phenyl, adamantyl, norbornanyl, phenethyl, $C_{4-6}$alkyl e.g. n-butyl, 3-methyl butyl, 3,3-dimethyl butyl, 1,3-dimethylbutyl, 2,3-dimethylbutyl, $C_{3-6}$hydroxy alkyl e.g. 2-hydroxypropyl, 2-hydroxy-3-methylbutyl, 2-hydroxy-3,3-dimethylbutyl, $C_{1-2}$alkyl substituted by a bridged $C_{7-10}$cycloalkyl group e.g. 2-norbornanylmethyl, 5-norbornenylmethyl, 2-adamantylmethyl, 2-adamantylethyl, 2-(1-adamantyl) ethyl, 1-adamantylmethyl, alkoxycarbonylalkyl, e.g. methoxycarbonylmethyl or t-butyoxycarbonylmethyl, or 2-cyclopentylethyl.

A particularly preferred class of compounds of formula (I) is that in which $R^1$ is 3-methyl-1-butyl or more especially adamantylmethyl.

A further preferred class of compounds are those wherein $R^2$ represents phenyl substituted by a group selected from $(CH_2)_nNR^4R^5$ (wherein n is 1 and $NR^4R^5$ represents a 5–7 membered saturated heterocylic ring e.g. morpholino, or n is zero $R^4$ is hydrogen and $R^5$ represents a $C^{1-6}$alkanoyl e.g. formyl or acetyl or $R^5$ represents $C_{2-4}$alkyl substituted by one or 2 hydroxy groups e.g. 2,3-dihydroxypropyl), $O(CH_2)_pCO_2R^7$ (wherein $R^7$ represents hydrogen or $C_{1-4}$alkyl e.g. ethyl and p is an integer from 2 to 4 e.g. 3) or $(CH_2)_nCO_2R^{11}$ wherein n is zero and more particularly $R^{11}$ is morpholinoethyl. Within this class of compounds those wherein the substituent is in the meta position in the phenyl ring are especially preferred.

Another preferred class of compounds are those wherein $R^3$ represents phenyl optionally substituted by fluorine e.g. phenyl or 2-fluorophenyl.

Compounds of formula (I) wherein X is NH represents a further preferred class of compounds.

A particular preferred group of compounds of formula are those wherein $R^1$ is 1-adamantylmethyl; $R^2$ is phenyl substituted by morpholinomethyl, formylamino, acetylamino, 2,3-dihydroxypropylamino, $O(CH_2)_3CO_2R^7$ wherein $R^7$ is H or ethyl, or $(CH_2)_nCO_2R^{11}$ wherein n is zero and $R^{11}$ represents morpholinoethyl; $R^3$ is phenyl; $R^{10}$ is hydrogen and X is NH; and more particularly the (+) enantiomers thereof.

Particularly preferred compounds of the invention include
(+)N-[1-(1-Adamantylmethyl)-2,4-dioxo-5-phenyl-2,3,4, 5-tetrahydro-1H-1,5-benzodiazepin-3-yl]-N'-[3-(4-morpholino methyl)phenyl]-urea;

(+)N-[1-(1-Adamantylmethyl)-2,4-dioxo-5-phenyl-2,3,4, 5-tetrahydro-1H-1,5benzodiazepin-3-yl]-N'-[4-[3-(ethoxycarbonyl)propyl-1-oxo]phenyl]urea (+)N-[1-(1-Adamantylmethyl)-2,4-dioxo-5-phenyl-2,3,4, 5-tetrahydro-1H-1,5benzodiazepin-3-yl]-N'-[4-(4-oxobutanoic acid)phenyl]urea (+)N-[1-(1-Adamantylmethyl)-2,4-dioxo-5-phenyl-2,3,4, 5-tetrahydro-1H-1,5-benzodiazepin-3-yl]-N'-[3-[2-(4-Morpholino)ethoxycarbonyl]phenyl]urea;

(+)N-[1-(1-Adamantylmethyl)-2,4-dioxo-5-phenyl-2,3,4, 5-tetrahydro-1H-1,5-benzodiazepin-3-yl]-N'-[3-(2,3-dihydroxypropylamino)phenyl]urea;

N-[1-(1-Adamantylmethyl)-2,4-dioxo-5-phenyl-2,3,4,5-tetrahydro-1H-1,5-benzodiazepin-3-yl]-N'-(3-formylaminophenyl)urea;

N-[1-(1-Adamantylmethyl)-2,4-dioxo-5-phenyl-2,3,4,5-tetrahydro-1H-1,5-benzodiazepin-3-yl]-N'-(3-acetamidophenyl)urea; and the (+) enantiomers thereof.

The pharmaceutically acceptable salts of the compounds of formula (I) include conventional salts formed for example from pharmaceutically acceptable inorganic or organic acids as well as quaternary ammonium acid addition salts. Examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts.

The compounds of formula (I) in which $R^7$ represents hydrogen may form pharmaceutically acceptable salts with suitable cations. Suitable pharmaceutically acceptable cations include alkali metal (e.g. sodium or potassium) and alkaline earth metal (e.g calcium or magnesium) cations.

For the groups $R^7$ and $R^{11}$ the term metabolically labile esters include substituted or unsubstituted aminoalkyl esters (e.g. aminoethyl, 2-(N,N-diethylamino) ethyl, or 2-(4-morpholino)ethyl esters) or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-methoxy-1-methyl-ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxycarbonyloxyethyl) or 1-(4-tetrahydropyranylcarbonyloxy)-ethyl.

The compound of formula (i) and salts and metabolically labile esters thereof may from solvates e.g. hydrates and the invention includes such solvates.

The compounds of the invention are potent and specific antagonists of gastrin and/or CCK and in particular gastrin and or CCK at the CCK-B-receptor. Thus compounds of the invention have been shown to be antagonists of CCK, particularly at CCK-B receptors as demonstrated for example by the compound's ability to inhibit the contractile actions of CCK-4 in the presence of a CCK-A antagonist, in the guinea-pig isolated ileum longitudinal muscle-myenteric plexus.

Compounds of the invention have also been found to have a significantly weaker activity at CCK-A receptors compared with their activity at gastrin and/or CCK-B receptors, as demonstrated by their ability to inhibit the contractile activity of CCK-8 in guinea-pig isolated ileum longitudinal muscle-myenteric plexus.

The preparation and use of guinea-pig isolated ileum longitudinal muscle-myenteric plexus has been described by K-H Buchheit et al in Nauyn-Schmeideberg's Arch. Pharmacol, (1985), 329, p36–41 and by V. L. Lucaites et al (1991) in J. Pharmacol. Exp. Ther., 256, 695–703.

The compounds of the invention have also been shown to be antagonists of gastrin as demonstrated by their ability to inhibit pentagastrin-stimulated acid secretion from rat isolated gastric mucosa using the procedure described by J. J. Reeves and R. Stables in *Br. J. Pharmacol.*, 1985, 86, p.677–684.

The greater affinity of the compounds of the invention for the CCK-B receptor over the CCK-A receptor has also been established using the CCK receptor binding assays described by G Dal Forno et al., J. Pharmcol. Exp & Ther. 261, 1056–1063, 1992.

The compounds of the invention are therefore useful for the treatment and/or prevention of disorders in mammals, especially humans, where modification of the effects of gastrin or CCK is of therapeutic benefit. Thus the compounds of the invention are useful for the treatment of central nervous system disorders where CCK and/or gastrin are involved. For example anxiety disorders (including panic disorder, agoraphobia, social phobia, simple phobia, obsessive compulsive disorders, post traumatic stress disorder, and general anxiety disorder), tardive dykinesia, depression, Parkinson's disease or psychosis. The compounds of the invention are also useful for the treatment of gastrointestinal disorders especially those where there is an advantage in lowering gastric acidity. Such disorders include peptic ulceration, reflux oesophagitis and Zollinger Ellison syndrome. They may also be useful for the treatment of gastrointestinal disorders such as irritable bowel syndrome, excess pancreatic secretion, acute pancreatitis, motility disorders, antral G cell hyperplasia, fundic mucosal hyperplasia or gastrointestinal neoplasms. They may also be useful for the treatment of dependency on drugs or substances of abuse and withdrawal, Gilles de la Tourette syndrome, or dysfunction of appetite regulatory systems; as well as the treatment of certain tumours of the lung, lower oesophagus, pancreas, stomach, intestines and colon. Compounds of the invention are also useful for directly inducing analgesia, or enhancing opiate or non-opiate mediated analgesia, as well as anaesthesia or loss of the sensation of pain.

The invention therefore provides a compound of formula (I) or a pharmaceutically acceptable salt or solvate thereof for use in therapy, in particular in human medicine.

According to another aspect the invention provides the use of a compound of formula (I) or a pharmaceutically acceptable salt or solvate thereof for the manufacture of a medicament for the treatment of conditions where modification of the effects of gastrin and/or CCK is of therapeutic benefit.

According to a further aspect of the invention we provide a method for the treatment of a mammal, including man, in particular in the treatment of conditions where modification of the effects of gastrin and/or CCK is of therapeutic benefit which method comprises administering an effective amount of a compound of formula (I) or a pharmaceutically acceptable salt or solvate thereof to the patient.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 0.01–2000 mg per day e.g 0.01–500mg per day.

The desired dose may conveniently be presented in a single dose or as divided doses administered at appropriate intervals, for example as two, three, four or more sub-doses per day.

Because the compounds of the invention antagonise the function of CCK in animals, they may also be used as feed additives to increase the food intake in animals in daily dosages of around 1 mg/kg to 10 mg/kg.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, or rectal administration. Oral administration is preferred.

Tablets and capsules for oral administration may contain conventional excipients such as binding agents, for example, syrup, accacia, gelatin, sorbitol, tragacanth, hydroxypropyl cellulose, mucilage of starch or polyvinylpyrrolidone; fillers, for example, lactose, sugar, microcrystalline cellulose, maize-starch, calcium phosphate or sorbitol; lubricants, for example, hydrogenated vegetable oils, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in prefilled syringes, vials and ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form which may be obtained by freeze drying for constitution with a suitable vehicle, e.g. sterile, pyrogen-free water, before use.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups $R^1$–$R^{11}$ are as defined for the compounds of formula (I) unless otherwise stated.

The compounds of formula (I) may be prepared by reaction of an amine of formula (II)

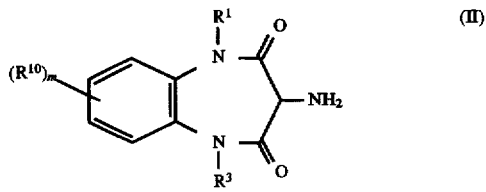

with an isocyanate (III) or an acyl chloride (IV)

$R^2NCO$                                                             (III)

$R^2XCOCl$                                                      (IV)

in which $R^2$ is as defined in formula (I) or is a group convertible thereto. The reaction conveniently takes place in the presence of a suitable solvent such as a halohydrocarbon e.g. dichloromethane, an ether e.g. tetrahydrofuran or a nitrile e.g. acetonitrile.

Compounds of formula (I) in which $R^5$ represents acyl or $C_{2-4}$alkyl substituted by hydroxy may be prepared from the corresponding compound of formula (I) wherein $R^2$ is phenyl substituted by an amino or aminoalkyl group. Thus compounds of formula (I) in which $R^5$ is acyl may be prepared by acylation of the corresponding compounds wherein $R^5$ is hydrogen by reaction with the appropriate acid halide, acid anhydride or mixed anhydride. For example compounds wherein $R^5$ is formyl may be prepared by reaction of the corresponding amino derivative with a mixture of formic acid and acetic anhydride. Compounds wherein $R^5$ is acetyl may be prepared by reaction of the corresponding amine with an acetyl halide e.g. chloride in the presence of a tertiary organic base such as triethylamine and optionally in a solvent e.g. dichloromethane.

Compounds wherein $R^5$ represents a $C_{2-4}$alkyl substituted by one or more hydroxyl groups may be prepared by alkylation or reductive alkylation of the corresponding compound wherein $R^5$ represents hydrogen. For example the alkylating agent may be an appropriate hydroxyalkyl halide or an epoxide. Alternatively the group $R^5$ may be introduced by a reductive alkylation using an appropriate aldehyde or ketone. Thus for example compounds of formula (I) in which $R^5$ represents 2,3-dihydroxypropyl may be prepared by reaction of the corresponding compound wherein $R^5$ is hydrogen with glyceraldehyde followed by reduction with sodium borohydride. Conveniently the reaction is carried out in a solvent such as ethanol or dichloromethane or a mixture thereof.

Compounds of formula (I) in which the group $CO_2R^7$ or $CO_2R^{11}$ are metabolically labile esters may be prepared from the corresponding acid by conventional techniques for preparing such esters. Thus the acid may be reacted with the appropriate alcohol in the presence of an acid activating agent such as carbonyl diimidazole. Conveniently the acid is reacted first with carbonyldimiidazole and the resultant imidazolide is then reacted with the appropriate alcohol. Preferably the reaction is carried out in a solvent e.g. toluene or tetrahydrofuran and with heating Compounds of the invention may be converted into other compounds of the invention. Thus compounds of formula (I) wherein $R^7$ is hydrogen may be prepared by hydrolysis of the corresponding compound of formula (I) wherein $R^7$ is alkyl. This hydrolysis may be carried out using aluminium triiodide in a solvent such as acetronitrile.

The compounds of formula (II) may be prepared by known methods e.g. as described in WO 93/14074.

In general, the compounds of formula (III) and (IV) are either known compounds or may be prepared according to methods used for the preparation of known compounds, Compounds of formula (I) contain at least one asymmetric carbon atom, namely the carbon atom of the diazepine ring to which the grouping $NHCOXR^2$ is attached. Specific enantiomers of the compounds of formula (I) may be obtained by resolution of the racemic compound using conventional procedures such as chiral HPLC. Alternatively the required enantiomer may be prepared by the corresponding enantiomer amine of formula (II) using any of the processes described above for preparing compounds of formula (I) from the amine (II). The enantiomers of the amine (II) may be prepared from the racemic amine (II) using conventional procedures such as salt formation with a suitably optically active acid such as R- camphorsulphonic acid.

The following examples, which are non-limiting, illustrate the invention.

In the Preparations and Examples, unless otherwise stated: Melting points (m.p.) were determined on a Buchi m.p. apparatus and are uncorrected. All temperatures refer to 0 C. Infrared spectra were measured in chloroform-$d_1$ solutions on a FT-IR instrument. Proton Magnetic Resonance (1H-NMR) spectra were recorded at 300 MHz as solutions in chloroform-$d_1$. Chemical shifts are reported in ppm downfield (d) from Me4Si as an interna I standard, and are assigned as singlets (s), doublets (d), doublet of doublets (dd) or multiplets (m). The following abbreviations are used in the text. EA=ethyl acetate, CH=cyclohexane, P=petroleum ether 40°–α C., THF=tetrahydrofuran, DCM= dichloromethane, EE=ethyl ether, DMF=N,N-dimethylformamide. Tlc refers to thin layer chromatography on silica plates. All the compounds are intended as racemic mixtures unless otherwise indicated.

Intermediate 1
(+)-1-(Adamantylmethyl)-3-amino-2,4-dioxo-5-phenyl2,3,4,5-tetrahydro-1H-1,5-benzodiazepine This compound and the corresponding racemate were prepared as described in WO93/14074

Intermediate 2
(+)N-[1-(Adamantylmethyl)-2,4-dioxo-5-phenyl-2,3,4,5-tetrahydro-1H-1,5-benzodiazepin-3-yl]-N'-(3-ethoxycarbonylphenyl)urea 3-Ethoxycarbonylphenyl isocyanate (0.152 ml) was added to a solution of intermediate 1 (0.490 g) in dry acetonitrile (20 ml) under a nitrogen atmosphere. The mixture was stirred at 23° for 1 h, then diluted with dichloromethane (20 ml) concentrated under vacuum and the residue was triturated with diethyl ether to give the title compound as a white solid (0.543 g). M.p. 220-1°. [alpha]$_D$=+60.8, (CHCl$_3$, c=1.020) T.l.c. CH-EA (2:1), Rf 0.35.

Intermediate 3
(+)N-[1-(1-Adamantylmethyl)-2,4-dioxo-5-phenyl-2,3,4,5-tetrahydro-1H-1,5benzodiazepin-3-yl]-N'-(3-carboxyphenyl)urea Aluminium iodide (0.137 g) was added to a suspension of Intermediate 2 (0.10 g) in dry acetonitrile (10 ml). The reaction mixture was stirred 6 h at 80° then cooled to 23° diluted with dichloromethane (30 ml) and poured into ice (10 g). The aqueous layer was acidified with a 10% solution of hydrochloric acid (1 ml), washed with 5% solution of sodium thiosulphate (20 ml) and extracted with dichloromethane (2×25 ml). The collected organic phases were washed with water (30 ml) and brine (10 ml) dried and evaporated to give a white solid (0.118 g). This material was purified on silica gel, eluted with CH/EA 1/1 and then EN/Methanol 1/1 to give the title compound (41 mg). T.l.c. EA, Rf 0.64.

Intermediate 4
N-[1-(1-Adamantylmethyl)-2,4-dioxo-5-phenyl-2,3,4,5-tetrahydro-1H-1,5-benzodiazepin-3-yl]-N'-(3-nitrophenyl)urea A solution of 3-nitrophenyl isocyanate (0.082 g) in dry acetonitrile (8 ml) was added to a solution of the 1-(1-Adamantylmethyl)-3-amino-2,4-dioxo-5-phenyl-2,3,4,5-tetrahydro-1H-1,5-benzodiazepine (0.2 g) in dry acetonitrile (10 ml) under a nitrogen atmosphere. The mixture was stirred at 23° for 2 h, then diluted with dichloromethane (15 ml) and washed with brine (15 ml). The organic solution was dried, concentrated in vacuo and the residue was triturated with diethyl ether to give the title compound as a white solid (0.229 g). M.p. 213°-5°. T.l.c. CH-EA (2:1), Rf0.33.

Intermediate 4a
In a similar manner (+)N-[1-(1-Adamantylmethyl)-2,4-dioxo-5-phenyl-2,3,4,5-tetrahydro-1H-1,5-benzodiazepin-3-yl]N'-(3-nitrophenyl)urea was prepared from intermediate 1 and 3-nitrophenyl isocyanate.

Intermediate 5
(+)N-[1-(1-Adamantylmethyl)-2,4-dioxo-5-phenyl-2,3,4,5-tetrahydro-1H-1,5-benzodiazepin-3-yl]-N'-(3-aminophenyl)urea 5% Pd/C (0.30 g) was added to a solution of (+)-(1-Adamantylmethyl)-2,4-dioxo-5-phenyl-2,3,4,5-tetrahydro-1H-1,5-benzodiazepin-3-yl]-N'-(3-nitrophenyl)urea (1.0 g) in dry THF (50 ml) and ethanol (50 ml) under a nitrogen atmosphere. The mixture was hydrogenated at 23° and 1 atm. for for 2h, then filtered and concentrated in vacuo; the residue was purified by flash chromatography (eluting with CH/EA 9/1); to give the title compound as a white solid (0.67 g). M.p..180° (dec). alpha$^D$=+38.3 T.l.c. EA/MeOH 3/1, R$_f$0.44 IR:3356(NH), 1707,1674 and 1639 (C=O), cm$^{-1}$; $^1$H-NMR:7.48(m); 7.39(m); 7.32(m); 7.15(m); 6.99 (m); 6.87(bs); 6.81(t); 6.51(m); 6.45(d); 6.35(m); 5.29(d); 4.49(d); 3.62(bs); 3.38(d); 1.86(m); 1.66–1.30(m).

Intermediate 5a
In a similar manner (1-Adamantylmethyl)-2,4-dioxo-5-phenyl-2,3,4,5-tetrahydro-1H-1,5-benzodiazepin-3-yl]-N'-(3-aminophenyl)urea was prepared from Intermediate 4.

EXAMPLE 1
(+)N-[1-(1-Adamantylmethyl)-2,4-dioxo-5-phenyl-2,3,4,5-tetrahydro-1H-1,5-benzodiazepin-3-yl]-N'-(3-(4-morpholinomethyl)phenyl]-urea To a solution of 3-(4-Morpholino)methylphenyl isocyanate (0.471 g) and triethylamine (0.017 ml) in acetonitrile (20 ml) a solution of the intermediate 1 (0.332 g) in dry acetonitrile (10 ml) was added. The mixture was stirred at 23° under a nitrogen atmosphere for 2 h, then diluted with dichloromethane (30 ml) and washed with brine (80 ml). The organic solution was dried, concentrated in vacuo and the residue was purified by flash chromatography using EA/MeOH 19/1 as eluent to give the title compound as a white solid (0.265 g). M.p. 175°-7° alpha$^d$=+39.8 T.l.c. EA, R$_f$0.38. IR:3292(NH); 1701, 1676 (C=O) cm$^{-1}$; $^1$H-NMR: 7.49(dd); 7.46–7.14(m); 7.026(bs); 6.99(dd); 6.74(d); 6.25 (m); 5.28(d); 4.49(d); 3.69(m); 3.43(s); 3.38(d); 2.42(m); 1.87(m); 1.70–1.30(m).

EXAMPLE 2
(+)N-[1-(1-Adamantylmethyl)-2,4-dioxo-5-phenyl-2,3,4,5-tetrahydro-1H-1,5-benzodiazepin-3yl]-N'-[4-(3-(ethoxycarbonyl)propyl-1-oxo)phenyl]urea 4-(4-isocyanate phenoxy)butyric acid, ethyl ester (0.353 g) in dry acetonitrile (20 ml) was added to the solution of the intermediate 1 (0.540 g) in dry acetonitrile (20 ml). The mixture was stirred at 23° under a nitrogen atmosphere for 24 h, concentrated in vacuo and the residue (0.78 g) taken up with DCM purified by flash chromatography (eluting in gradient from CH-EA 3:1 to CH-EA 3:2 to give a compound (0.610 g), which was triturated with diethyl ether to give the pure title compound (0.551 g) M.p. 255.5°–6.5°(dec). T.l.c. CH/EA(1/1), R$_f$0.55. alpha$^D$=+25.7 IR: 3400–3333(NH), 1736, 1699 and 1651 (C=O) cm$^{-1}$; $^1$H-NMR: 7.48(dd); 7.45–7.2(m); 7.16(tt); 6.99(dd); 6.83(d); 6.39(bs); 6.1(d); 5.25(d); 4.48(d); 4.14(q); 3.97(t); 3.38(d); 2.51(t); 2.09(m); 1.87(m); 1.68–1.34(m); 1.26(t).

EXAMPLE 3
(+)N-[1-(1-Adamantylmethyl)-2,4-dioxo-5-phenyl-2,3,4,5-tetrahydro-1H-1,5benzodiazepin-3-yl]-N'-[4-(4-oxobutanoic acid)phenyl]urea Aluminum triiodide (1656g) was added to the solution of (+)N-[1-(1-Adamantylmethyl)-2,4-dioxo-5-phenyl-2,3,4,5-tetrahydro-1H-1,5benzodiazepin-3-yl]-N'-[4-(3-(ethoxycarbonyl)propyl-1-oxo)phenyl]urea (0.513 g) in dry acetonitrile (50 ml). The reaction mixture was stirred at reflux for 2 h, then concentrated in vacuo and the residue dissolved in DCM (100 ml) and washed with 10% hydrochloric acid solution (2×80 ml), 5% sodium hydrogen carbonate solution, 10% hydrochloric acid solution (80 ml), water (2×80 ml), brine (2×80 ml) 5% sodium sodium dithionite (2×80 ml) and brine (2×80 ml). The organic extracts were dried and concentrated in vacuo and the residue (0.841 g) purified by flash chromatography (eluting in gradient from CH-EA 3:2 to DCM-MeOH 9:1 and finally to DCM-MeOH4:1) to give the title compound as a white solid (0.182 g) M.p. 195°–205° (dec). T.l.c. EA, $R_f$0.39. IR: 3281(NH and OH), 1695 and 1668 (C=O) cm$^{-1}$; $^1$H-NMR:12.1(m); 8.96(s); 7.82(m); 7.49(t); 7.37(m); 7.28 (m); 4.99(d); 7.22(d); 6.94(dd); 6.79(d); 4.98(d); 4.28(d); 3.88(t); 3.60(d); 2.32(t); 1.87(m); 1.84(m); 1.66–1.22(m).

EXAMPLE 4

(+)N-[1-(1-Adamantylmethyl)-2,4-dioxo-5-phenyl-2,3,4,5-tetrahydro-1H-5-benzodiazepin-3-yl]-N'-[3-[2-(4-Morpholino)ethoxycarbonyl]phenyl]urea To a solution of Intermediate 3 (0.10 g) in dry THF (5 ml) N,N'-carbonyl diimidazole (0.056 g) was added and the reaction mixture was stirred at 20° for 20 h. The solvent was evaporated and the residue taken up in toluene; N-(2-hydroxyethyl)morpholine (0.069 g) was then added and stirring was continued for 16 h at 20° and at reflux for 4 h. The reaction mixture was dried, concentrated in vacuo and the residue was taken up with DCM (50 ml) and washed with saturated ammonium chloride solution (30 ml) and brine (2×40 ml) to give a crude compound (0.15 g) which was purified by preparative t.l.c using CH/MeOH 95/0.5 as eluent to give the title compound as a white solid (0.03 g). T.l.c. CH-EA(2:1). $R_f$=0.2 IR:3400(NH), 1718 (C=O)cm$^{-1}$; $^1$H-NMR: 7.91(bs); 7.58(d); 7.54–7.06(m); 7.00(dd); 6.65 (m); 5.27(m); 4.54–4.38(m); 3.73(t); 3.38(d); 2.79(t); 2.61 (m); 1.87(m); 2.2–1.3(m).

EXAMPLE 5

(+)N-[1-(1-Adamantylmethyl)-2,4-dioxo-5-phenyl-2,3,4,5-tetrahydro-1H-1,5-benzodiazepin-3-yl]N'-[3-(2,3-dihydroxypropylamino)phenyl]urea To the solution of D-(+)-Glyceraldehyde (0.22 g) and the intermediate 5 (0.135 g) in ethanol (3 ml) and dichloromethane (2 ml) at 23°, acetic acid (0.013 ml), sodium acetate trihydrate (0.040 g) and water (1 ml) were added.

Sodium borohydride was then added portionwise during 30 min. and stirring continued for 3 h at 23°. After evaporation under vacuum the residue was treated with the same quantities of reagents under the same conditions. The reaction mixture was concentrated under vacuum, the residue taken up in dichloromethane (50 ml) and washed with water (20 ml) and brine (20 ml). The organic solution was dried, concentrated in vacuo and the residue was purified by flash chromatography on silica using CH/EA 1/1 and then methanol to give the title compound as a white solid (0.053 g). T.l.c. EA/MeOH 7/3 Rf=0.64. IR cm$^{-1}$ $^{3377}$ (NH,OH), 1705, 1659 (C=O), 1610 (C=C); $^1$H-NMR:7.53(bs); 7.46(d); 7.42–7.22(m); 7.14(m); 6.97(m); 6.74(d); 6.64(s); 6.62(d); 6.26(d); 5.26(d); 4.44(d); 3.80(m); 3.64–3.44(m); 3.35(d); 3.20–2.98(m); 1.86(m); 1.70–1.3(m).

EXAMPLE 6

N-[1-(1-Adamantylmethyl)-2,4-dioxo-5-phenyl-2,3,4,5-tetrahydro-1H-1,5-benzodiazepin-3-yl]-N'-(3-formylaminophenyl)urea To a solution of Intermediate 5a in formic acid (2 ml), acetic anhydride (0.7 ml) was added, and the reaction mixture was stirred at 15° for 3 h then at 20° for 20 h. It was concentrated under vacuum, taken up with DCM (50 ml) and purified by flash chromatography, using CH/EA 1/1 as eluants to give a residue which was crystallised using DCM/Petroleum to give the title compound as a white solid (0.097 g) T.l.c. CH-EA (1/9) $R_f$=0.54. IR:3341 (NH), 1703 and 1645 (C=O), 1609 (C=C) cm$^{-1}$; $^1$H-NMR:8.58(m); 8.10(bs); 7.78(bs); 7.76(bs); 7.69(bd); 7.50-(m); 7.43–7.22 (m); 7.20–7.04(m); 7.00(dd); 6.96(dd); 6.88(bd); 6.83(bd); 6.60(dd); 5.27(d); 4.47(m); 3.35(m); 1.82(m); 1.64–1.30(m).

EXAMPLE 7

N-[1-(1-Adamantylmethyl)-2,4-dioxo-5-phenyl-2,3,4,5-tetrahydro-1H-1,5-benzodiazepin-3-yl]-N'-(3-acetamidophenyl)urea Acetyl chloride (0.011 g) was added to the intermediate 5a(0.07 g) in DCM (4 ml) and triethylamine (0.010 g).

The mixture was stirred at 23° for 1 h, then filtered. The solid obtained was dissolved in DCM (70 ml) and washed with water (30 ml), 20% sodium hydroxide solution (30 ml), 5% hydrocloric acid (30 ml) and water (30 ml), dried and concentrated under vacuum, to give the title compound as a white solid (0.050 g) tl.c. EA/MeOH 9/1 Rf=0.82

IR:3346 (NH), 1701 and 1684 (C=O), 1607, 1558 (C=C)cm$^{-1}$; $^1$H-NMR:9.83(bs); 9.17(bs); 7.83(d); 7.64 (bs); 7.54(t); 7.36(t); 7.34(m), 7.06(m); 6.98–6.90(m); 4.99 (d); 4.30(d); 3.60(d); 1.99(s); 1.84(bs); 1.70–1.2(m).

Pharmacy Example

| Capsules or Tablets | mg/dosage form |
| --- | --- |
| Active ingredient | 0.1 |
| Polyethyleneglycol | 15.0 |
| Lactose | 52.4 |
| Starch | 30.0 |
| Magnesium stearate | 0.5 |
| Silicon dioxide | 1.0 |
| Sodium Lauryl Suphate | 1.0 |
| | 100.0 |

The active ingredient is dispersed in a suitable solvent (e.g. ethanol) together with polyethyleneglycol. The solvent is removed. The powder so obtained is blended with the other excipients. The blend can be used to fill gelatine capsules or compressed using appropriate punches. The tablets can be coated using conventional techniques and coatings.

| Active ingredient | 0.1 |
| --- | --- |
| Povidone | 15.4 |
| Lactose | 74.0 |
| Hydrogenated vegetable oils | 3.0 |
| Silicon dioxide | 1.0 |
| Sodium Laauryl sulphate | 1.5 |
| Crospovidone | 5.0 |
| | 100.0 |

The active ingredient is dispersed in a suitable solvent (e.g. ethanol) together with povidone. The solution is sprayed on to lactose and the solvent removed. The powder obtained is blended with the other excipients. The blend is used to fill gelatine capsules or comprssed using appropriate punches. The tablet can be coated using conventional techniques and coatings.

Oral liquid

| Active ingredient | 70–100 micrograms/dose |
| --- | --- |
| ethanol | 5–15% |

-continued

| | |
|---|---|
| Sodium saccharinate | 0.1–1% |
| Propylene glycol | 10–100% |
| Purified water | qb 100% |
| Pack; plastic or glass bottle or other suitable pack | |

Injection Formulation

| | |
|---|---|
| Active ingredient | 0.1–100 micrograms |
| Sodium phosphate | 1.50 mg/ml |
| NaOH | qs desired pH (range 3–9) |
| propylene glycol | 10–500 mg/ml |
| water for injection | qs to 0.5–10 ml |

CCK—Receptor Binding

The binding affinity of the compounds of the invention for the CCK-A receptor (Pancreas Assay) and CCK-B receptor (guinea pig cortex assay) was determined using the procedure of G Dal Forno et al J. Pharmacol. Exp & Ther. 261—1056–1063. The pKi values determined with respresentative compounds of invention were as follows:

| | pKi | |
|---|---|---|
| Compound Ex No | CCK-A | CCK-B |
| 1 | 4.70 | 8.52 |
| 2 | <5.0 | 8.28 |
| 3 | <5.0 | 8.42 |
| 4 | 6.47 | 9.25 |
| 5 | 5.13 | 9.17 |
| 6 | 5.95 | 9.02 |
| 7 | 5.82 | 8.88 |

The compounds of the invention are essentially non-toxic and therapeutically useful doses.

We claim:

1. A compound of formula (I)

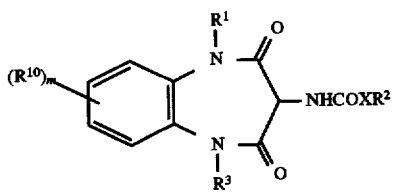

wherein $R^1$ represents a phenyl, $C_{3-7}$cycloalkyl, $C_{7-11}$bridgedcycloalkyl or $C_{1-6}$alkyl group which alkyl group may be substituted by a hydroxy, phenyl, $C_{1-6}$alkoxycarbonyl, $C_{3-7}$cycloalkyl, or $C_{7-11}$bridgedcycloalkyl group;

$R^2$ represents phenyl substituted by a group $(CH_2)_n NR^4R^5$, $O(CH_2)_p R^6$, or $(CH_2)_n CO_2 R^{11}$;

$R^3$ represents phenyl optionally substituted by one or 2 halogen atoms;

$R^4$ represents hydrogen or $C_{1-4}$alkyl;

$R^5$ represents acyl, or $C_{2-4}$alkyl substituted by one or more hydroxy; carboxyl and/or amino groups, or $R^4$ and $R^5$ together with the nitrogen atom to which they are attached form a 5–7 saturated heterocyclic ring which contain an additional heteroatom selected from oxygen, sulphur or nitrogen and/or may be substituted by 1 or 2 $C_{1-4}$alkyl or hydroxy groups;

$R^6$ represents hydroxy, $C_{1-4}$alkoxy, $CO_2 R^7$ or $NR^8 R^9$;

$R^7$ represents hydrogen or $C_{1-4}$alkyl or a metabolically labile ester group;

$R^8$ represents hydrogen, $C_{1-4}$alkyl, acyl or $C_{2-6}$alkyl substituted by one or more hydroxy, carboxyl and/or amino groups or $R^8$ and $R^9$ together with the nitrogen atom to which they are attached form a 5–7 saturated heterocyclic ring which contain an additional heteroatom selected from oxygen, sulphur or nitrogen and/or may be substituted by 1 or 2 $C_{1-4}$alkyl or hydroxy groups;

$R^{10}$ represents hydrogen or a halogen atom; $R^{11}$ represents a metabolically labile ester group; m is zero, 1 or 2;

n is zero or 1; p is an integer from 1 to 4; X represents oxygen or NH and pharmaceutically acceptable salts thereof.

2. A compound as claimed in claim 1 wherein X is NH.

3. A compound as claimed in claim 1 or wherein $R^1$ represents 1-adamantylmethyl.

4. A compound as claimed in claim 1 wherein $R^3$ represents phenyl or 2fluorophenyl.

5. A compound as claimed in claim 1 wherein $R^{10}$ represents hydrogen.

6. A compound as claimed in claim 1 wherein $R^2$ represents phenyl substituted by a group selected from $(CH_2)_n NR^4 R^5$ (wherein n is 1 and $NR_4 R^5$ represents a 5–7 membered saturated heterocylic ring, or n is zero, $R^4$ is hydrogen and $R^5$ represents a $C_{1-6}$alkanoyl or $R^5$ represents $C_{2-4}$alkyl substituted by one or 2 hydroxy groups), $O(CH_2)_p CO_2 R^7$ (wherein $R^7$ represents hydrogen or $C_{1-4}$alkyl and p is an integer from 2 to 4) or $(CH_2)_n CO_2 R_{11}$ wherein n is zero.

7. A compound as claimed in claim 1 wherein $R^2$ is phenyl substituted by morpholinomethyl, formylamino, acetylamino, 2,3-dihydroxypropylamino, $O(CH_2)_3 CO_2 R^7$ wherein n is zero and $R^7$ is hydrogen or ethyl, or $(CH_2)_n CO_2 R^{11}$ wherein n is zero and $R^{11}$ is morpholinoethyl.

8. The compounds:

(+)N-[1-(1-Adamantylmethyl)-2,4-dioxo-5-phenyl-2,3,4,5-tetrahydro-1H-1,5-benzodiazepin-3-yl]-N'-[3-(4-morpholino methyl)phenyl]-urea;

(+)N-[1-(1-Adamantylmethyl)-2,4-dioxo-5-phenyl-2,3,4,5-tetrahydro-1H-1,5-benzodiazepin-3-yl]-N'-[4-[3-(ethoxycarbonyl)propyl-1-oxo]phenyl]urea (+)N-[1-(1-Adamantylmethyl)-2,4-dioxo-5-phenyl-2,3,4,5-tetrahydro-1H-1,5-benzodiazepin-3-yl]-N'-[4-(4-oxobutanoic acid)phenyl]urea (+)N-[1-(1-Adamantylmethyl)-2,4-dioxo-5-phenyl-2,3,4,5-tetrahydro-1H-1,5-benzodiazepin-3-yl]-N'-[3-[2-(4Morpholino)ethoxycarbonyl]phenyl]urea;

(+)N-[1-(1-Adamantylmethyl)-2,4-dioxo-5-phenyl-2,3,4,5-tetrahydro-1H-1,5-benzodiazepin-3-yl]-N'-[3-(2,3-dihydroxypropylamino)phenyl]urea;

N-[1-(1-Adamantylmethyl)-2,4-dioxo-5-phenyl-2,3,4,5-tetrahydro-1H-1,5-benzodiazepin-3-yl]-N'-(3-formylaminophenyl)urea;

N-[1-(1-Adamantylmethyl)-2,4-dioxo-5-phenyl-2,3,4,5-tetrahydro-1H-1,5-benzodiazepin-3-yl]-N'-(3-acetamidophenyl)urea; and the (+) enantiomers thereof.

9. Pharmaceutical compositions comprising a compound as claimed in claim 1 in admixture with one or more physiologically acceptable carriers or excipients.

10. A method of treatment of a mammal including man for conditions where modification of the effect of gastrin and or CCK is of therapeutic benefit comprising administration of an effective amount of a compound as claimed in claim 1.

* * * * *